(12) United States Patent
Hicks et al.

(10) Patent No.: US 11,135,147 B2
(45) Date of Patent: Oct. 5, 2021

(54) SKIN CARE COMPOSITION AND METHOD THEREOF

(71) Applicant: THE BOOTS COMPANY PLC, Nottingham (GB)

(72) Inventors: Jake Thomas Hicks, Nottingham (GB); Paul James Tomlinson, Derby (GB)

(73) Assignee: THE BOOTS COMPANY PLC, Nottingham (GB)

( * ) Notice: Subject to any disclaimer, the term of this patent is extended or adjusted under 35 U.S.C. 154(b) by 258 days.

(21) Appl. No.: 16/312,928

(22) PCT Filed: Jun. 28, 2017

(86) PCT No.: PCT/EP2017/025185
§ 371 (c)(1),
(2) Date: Dec. 21, 2018

(87) PCT Pub. No.: WO2018/001573
PCT Pub. Date: Jan. 4, 2018

(65) Prior Publication Data
US 2019/0328645 A1  Oct. 31, 2019

(30) Foreign Application Priority Data

Jun. 30, 2016 (GB) ..................... 1611362

(51) Int. Cl.
| | | |
|---|---|---|
| A61K 8/67 | (2006.01) | |
| A61K 8/06 | (2006.01) | |
| A61K 8/368 | (2006.01) | |
| A61Q 19/00 | (2006.01) | |
| A61Q 19/02 | (2006.01) | |
| A61Q 19/08 | (2006.01) | |
| A61Q 19/10 | (2006.01) | |

(52) U.S. Cl.
CPC ............. *A61K 8/676* (2013.01); *A61K 8/062* (2013.01); *A61K 8/368* (2013.01); *A61Q 19/007* (2013.01); *A61Q 19/02* (2013.01); *A61Q 19/08* (2013.01); *A61Q 19/10* (2013.01)

(58) Field of Classification Search
CPC ................................................... A61K 8/676
See application file for complete search history.

(56) References Cited

U.S. PATENT DOCUMENTS

| | | |
|---|---|---|
| 4,970,252 A | 11/1990 | Sakuta et al. |
| 5,412,004 A | 5/1995 | Tachibana et al. |
| 5,520,918 A | 5/1996 | Smith |
| 5,654,362 A | 8/1997 | Schulz, Jr. et al. |
| 5,760,116 A | 6/1998 | Kilgour et al. |
| 5,811,487 A | 9/1998 | Schulz, Jr. et al. |
| 5,837,793 A | 11/1998 | Harashima et al. |
| 6,447,817 B1 | 9/2002 | Niyiro et al. |
| 2003/0045572 A1 | 3/2003 | Niyiro et al. |
| 2007/0025937 A1 | 2/2007 | Fares et al. |
| 2014/0155633 A1 | 6/2014 | Chen et al. |
| 2018/0318202 A1 * | 11/2018 | Tomlinson ............. A61K 8/042 |
| 2019/0314648 A1 * | 10/2019 | Sitaram ................. A61K 8/498 |

FOREIGN PATENT DOCUMENTS

| | | | |
|---|---|---|---|
| EP | 1106175 A1 | 6/2001 | |
| EP | 2722043 A1 | 4/2014 | |
| JP | H0782135 A | 3/1995 | |
| JP | H08501553 A | 2/1996 | |
| JP | 03153609 A * | 7/1999 | |
| KR | 20010079630 A | 8/2001 | |
| WO | WO-99/26572 A1 | 6/1999 | |
| WO | WO-2007/118605 A1 | 10/2007 | |
| WO | WO-2007118605 A1 * | 10/2007 | ............. A61K 8/368 |

OTHER PUBLICATIONS

"Brightening Concentrated Lotion", Database GNPD Mintel, Database Accession No. 3957043 (May 31, 2016).
Drops of Light™ Pure Healthy Brightening Serum, The Body Shop, downloaded from the Internet at: <https://web.archive.org/web/20160324100114/http:/www.thebodyshop.ca/en/skin-care/facial-serums/drops-of-light-brightening-serum.aspx> (available online Mar. 24, 2016).
Great Britain Patent Application No. GB1611362.3, Search Report under Section 17, dated Mar. 17, 2017.
International Application No. PCT/EP2017/025185, International Preliminary Report on Patentability (Chapter II), dated Sep. 13, 2018.
International Application No. PCT/EP2017/025185, International Search Report and Written Opinion, dated Oct. 10, 2017.
REMEDY Spot Treatment Blemish and Dark Spot Corrector, downloaded from the Internet at: <https://www.everskin.com/with/stephanie/products/744-remedy-spot-treatment?style=1552> (access Mar. 17, 2017).
Yatskayer et al., Evaluation of the efficacy and tolerance of a whitening sheet mask alone and in combination with a whitening serum on Asian panel, downloaded from the internet at: <http://www.congress.loreal.com/2015-wcd/kielhs_2984317_new_without_logo.pdf> (Accessed Mar. 17, 2017).

* cited by examiner

*Primary Examiner* — Gina C Justice
(74) *Attorney, Agent, or Firm* — Marshall, Gerstein & Borun LLP

(57) ABSTRACT

The disclosed technology relates to a composition comprising: 0.1 to 3 wt % (or 0.5 to 2.5 wt %) of a beta hydroxy acid, 0.05 to 3 wt % (or 0.09 to 2.5 wt %) of an O-substituted ascorbic acid or a derivative thereof, and a cosmetically acceptable medium comprising an aqueous phase, wherein a beta hydroxy acid is present at a higher concentration than O-substituted ascorbic acid or a derivative thereof. The disclosed technology further relates to the use and method of improving skin condition.

14 Claims, No Drawings

SKIN CARE COMPOSITION AND METHOD THEREOF

TECHNICAL FIELD

The disclosed technology relates to a composition comprising: 0.1 to 3 wt % (or 0.5 to 2.5 wt %) of a beta hydroxy acid, 0.05 to 3 wt % (or 0.09 to 2.5 wt %) of an O-substituted ascorbic acid or a derivative thereof, and a cosmetically acceptable medium comprising an aqueous phase, wherein a beta hydroxy acid is present at a higher concentration than O-substituted ascorbic acid or a derivative thereof. The disclosed technology further relates to the use and method of improving skin condition.

BACKGROUND OF THE INVENTION

Vitamin C and salicylic acid are ingredients known for use in cosmetics and/or personal care formulations.

Salicylic acid is known to improve skin thickness, barrier function, and collagen production. Salicylic acid is also known as a treatment for blemishes or acne, as well as being an antimicrobial agent. The effectiveness of salicylic acid is believed to be optimal at lower pH conditions.

Compositions are known to contain 3-O-ethyl ascorbic acid and salicylic acid as is evidenced by Mintel records, for example: The Body Shop product "Drops of Light Pure Healthy Brightening Serum" (Record ID 3926549), and Shiseido product "Benefique AC Acne Spots Serum" (Record ID 3673921). The person skilled in the art knows that for a composition having an INCI list that ingredients featured higher in a list are present at higher concentrations than ingredients listed thereafter. Both Mintel records list 3-O-ethyl ascorbic acid higher in the list than salicylic acid, indicating that 3-O-ethyl ascorbic acid is present in a higher amount than salicylic acid. Compositions such as these are believed to have a higher pH since the compositions contain less salicylic acid.

However, as a composition pH decreases, the stability of compositions comprising Vitamin C, or a derivative thereof (such as ascorbyl phosphate and ascorbyl glucoside) are believed to become less stable. As a result compositions containing greater concentrations of strong acids exacerbate the stability problem of vitamin C or derivatives thereof.

However, given the benefits Vitamin C and various derivatives in cosmetic and/or personal care formulations that include enhanced collagen synthesis, or as an antioxidant and has been used in compositions for anti-ageing (through reduced wrinkle, fine lines or improving skin firmness), and providing brighter/radiant skin. Compositions containing Vitamin C or its derivatives have also been suggested to reduce the appearance of brown spots and other types of sun damage, and to improve skin's natural healing response. In one embodiment it would be desirable to use a form of vitamin C in compositions that may have a low pH.

SUMMARY OF THE INVENTION

It would be advantageous to prepare a composition comprising a beta hydroxy acid and a form of Vitamin C to improve skin care condition (this may also be referred to as skin condition). Improved skin care may include at least one of the following: improving skin exfoliation, improved moisturisation, reducing wrinkle formation or fine lines, reducing skin sagging or hyperpigmentation (such as solar lentigines), increasing skin firmness or skin laxity and reducing blemishes. The composition may also provide efficacy in preventing or relieving the symptoms of sensitive skin or towards skin sensitizing agents by improving its resistance to the triggering factors.

However, due to the difference in the believed optimum functional conditions outlined above it would be advantageous to have a composition having improved stability due to enhanced stability of the form of Vitamin C in a composition comprising a beta hydroxy acid.

As used herein, the transitional term "comprising," which is synonymous with "including," "containing," or "characterized by," is inclusive or open-ended and does not exclude additional, un-recited elements or method steps. However, in each recitation of "comprising" herein, it is intended that the term also encompass, as alternative embodiments, the phrases "consisting essentially of" and "consisting of," where "consisting of" excludes any element or step not specified and "consisting essentially of" permits the inclusion of additional un-recited elements or steps that do not materially affect the basic, essential and novel characteristics of the composition, method or use under consideration.

Unless otherwise indicated treat rates are on a weight basis relative to the total composition disclosed herein.

Unless otherwise indicated various ingredients disclosed herein may be individual compounds, or in a mixture of compounds.

In one embodiment the disclosed technology relates to a composition comprising: 0.1 to 3 wt % (or 0.5 to 2.5 wt %) of a beta hydroxy acid, 0.05 to less than 3 wt % (or 0.09 to less than 2.5 wt %) of an O-substituted ascorbic acid or a derivative thereof, and a cosmetically acceptable medium comprising an aqueous phase, wherein a beta hydroxy acid is present at a higher concentration than O-substituted ascorbic acid or a derivative thereof.

The cosmetically acceptable medium may be in the form of an emulsion, or a gel. The emulsion may be a water-in-oil, oil-in-water, or water-in-silicone.

If the composition disclosed herein is in the form of a gel, the gel may be a mono-phase gel, or a multi-phase gel.

The composition may have a weight ratio of beta hydroxy acid to O-substituted ascorbic acid or a derivative thereof of 1:to less than 1, to 1:0.01, or the weight ratio may be 1:0.7 to 1:0.5, or the weight ratio may be 1:0.5 to 1:0.1.

The composition disclosed herein may have a pH ranging from 3 to 7, or 4.0 to 5.5.

In one embodiment the disclosed technology relates to a composition comprising salicylic acid as the beta hydroxy acid, and 3-O-ethyl ascorbic acid as the O-substituted ascorbic acid or a derivative thereof.

The composition may be in the form of a gel, cream, lotion or serum, typically a cream, serum, lotion. In one embodiment the composition may be a serum.

The composition may be an emulsion or gel.

In one embodiment the disclosed technology relates to a method of improving skin care comprising applying (such as topically applying) to skin the composition disclosed herein. Improving skin care may include improving (i) skin exfoliation, or moisturisation, or (ii) decreasing or preventing at least one of the following: forming wrinkles or fine lines, skin sagging, or hyperpigmentation (such as solar lentigines), or (iii) increasing skin firmness or skin laxity.

In one embodiment the disclosed technology relates to a method for treating sensitive or allergic skin by applying (such as topically applying) to skin the composition disclosed herein.

In one embodiment the disclosed technology relates to the use of the composition disclosed herein to improve skin care. Improved skin care may include improving (i) skin exfoliation, or moisturisation, or (ii) decreasing or preventing at least one of the following: forming wrinkles or fine lines, skin sagging, or hyperpigmentation (such as solar lentigines), or (iii) increasing skin firmness or skin laxity. Improved skin care may include reducing allergies.

The use and method disclosed herein are known to the skilled person as not encompassing therapeutic or medical treatment i.e., the disclosed use or method relate to a non-therapeutic use or method.

In one embodiment skin is a mammalian skin such as human skin.

DETAILED DESCRIPTION OF THE INVENTION

The disclosed technology provides a composition, methods and uses as disclosed above.

Beta Hydroxy Acid

The compositions disclosed comprises a beta hydroxy acid, or a salt or derivative thereof.

The term "beta hydroxy acid" (or β-hydroxy acid (BHA)) is used to define an organic compound that contains a carboxylic acid functional group and a hydroxy functional group separated by two carbon atoms.

The BHA may be in the form of a salt, or ester, or amide, or acid. In different embodiments the BHA may be an ester or acid.

The BHA may be aromatic, or acyclic or linear. In one embodiment the BHA is aromatic.

The BHA may include salicylic acid, or salts thereof. The salts of salicylic acid may include calcium salicylate, magnesium salicylate, MEA-salicylate, potassium salicylate, sodium salicylate, TEA-salicylate).

In one embodiment the BHA may be aromatic, and an example includes salicylic acid.

In one embodiment the BHA may be linear, and examples include beta-hydroxybutyric acid, or beta-hydroxy beta-methylbutyric acid.

O-Substituted Ascorbic Acid

The O-substituted ascorbic acid or a derivative thereof may be an O-alk(en)yl ascorbic acid or a derivative thereof.

As used herein "alk(en)yl" is intended to mean alkyl or alkenyl (typically alkyl).

The alk(en)yl may be acyclic or cyclic, typically acyclic. The acyclic group may be linear or branched, typically linear.

Typically the O-substituted ascorbic acid or a derivative thereof may be an O-alkyl ascorbic acid, or a derivative thereof.

The O-substituted ascorbic acid, or a derivative thereof is known in the art, and described in EP Patent application EP2722043 A1, and US 2014/0155633 (both Lin et al., Applicant Corum).

In one embodiment the O-substituted ascorbic acid, or a derivative thereof may be represented by the formula:

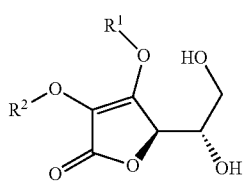

wherein $R^1$ and $R^2$ groups may independently be H, C1-20 alkyl, C3-20 cycloalkyl, C1-20 alkoxy, C2-20 acyl, C6-20 aryl, C1-20 heterocyclic aromatic, C1-20 heterocyclic non-aromatic, or C3-20 cycloalkenyl, with the proviso that both $R^1$ and $R^2$ cannot be H (i.e. with the proviso that the O-substituted ascorbic acid cannot be ascorbic acid in its unsubstituted form).

The O-substituted ascorbic acid or a derivative thereof may have a substituted group that may be hydrocarbon in nature i.e., composed on carbon and hydrogen. In one embodiment $R^1$ and $R^2$ groups may independently be H, C1-20 alkyl, C3-20 cycloalkyl, C6-20 aryl, or C3-20 cycloalkenyl, with the proviso that both $R^1$ and $R^2$ cannot be H.

In one embodiment the O-substituted ascorbic acid may be 3-alkyl ascorbic acid, or mixtures thereof. Typically the alkyl group may be a C1-20, or C1-10, or C2-8, or C2-4.

Typically the O-substituted ascorbic acid may be 3-O-ethyl ascorbic acid.

In one embodiment the composition disclosed herein does not include gluconolactone.

Other Ingredients

The composition disclosed herein may optionally further comprise other ingredients. The other ingredients include *Hibiscus*, a peptide, a matrix metalloproteinase inhibitor (MMPi), a whitening agent, a skin conditioning agent, a sunscreen agent, preservatives thickeners, viscosity modifying agents, and/or gelling agents sequestering agents, wax, diluents, carriers, propellants perfumes, or pH adjusting agents.

In one embodiment the composition disclosed herein further comprises one or more of *Hibiscus*, a peptide, an MMPi and a whitening agent.

The *Hibiscus* may be *Hibiscus sabdariffa, Hibiscus rosa sinensis* or *Hibiscus Abelmoschus*. All three *Hibiscus* plants are known to form extracts used in cosmetic compositions. The *Hibiscus* may be in the form of an extract.

Peptides are defined as compounds comprising an uninterrupted sequence of amino acids. For example the peptides are of natural origin. A dipeptide comprises an uninterrupted sequence of two amino acids. Amino acids, as employed herein, include and encompass all of the naturally occurring amino acids, either in D or L configuration. Amino acids are commonly indicated with reference to the conventional three letter code and the sequence is read from left to right. The composition of the disclosed technology may include a dipeptide chosen from acetyl dipeptide 1 cetyl ester, acetyl dipeptide 3 aminohexanoate, azelaoyl bisdipeptide 10, coumaroyl dipeptide 3, dicetyl dipeptide 9, dipeptide diamino butyroyl benzylamide diacetate, dipeptide 1, dipeptide 10, dipeptide 11, dipeptide 12, dipeptide 15, dipeptide 16, dipeptide 17, dipeptide 18, dipeptide 19, dipeptide 2, dipeptide 20, dipeptide 3, dipeptide 4, dipeptide 5, dipeptide 6, dipeptide 7, dipeptide 8, dipeptide 8 HCL, dipeptide 9, hexanoyl dipeptide 3 norleucine acetate, methyl undecylenoyl dipeptide 16, nicotinoyl dipeptide 22, nicotinoyl dipeptide 23, nicotinoyl dipeptide 24, nicotinoyl dipeptide 26, oleoyl dipeptide 15, palmitoyl dipeptide 10, palmitoyl dipeptide 13, palmitoyl dipeptide 17, palmitoyl dipeptide 5 diaminobutyroyl hydroxythreonine, palmitoyl dipeptide 5 diaminohydroxy butyrate, palmitoyl dipeptide 7 and mixtures thereof.

In one embodiment the composition of the disclosed technology may include a tripeptide, or mixtures thereof. The tripeptide may be naturally occurring or of synthetic origin. Suitable tripeptide compounds include tripeptide 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, derivatives thereof, and mixtures thereof. The tripeptide comprise one or more His-based tripeptides.

The compositions of the disclosed technology may further comprise a tetrapeptide. The tetrapeptide may be one or more rigin-based tetrapeptides, one or more ALAMCAT-tetrapeptides or mixtures thereof. The tetrapeptide may be naturally occurring or of synthetic origin. Suitable tetrapeptides for use in the present composition include those chosen from tetrapeptide 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 34, 35, derivatives thereof and mixtures thereof.

Rigin-based tetrapeptides of the disclosed technology may be based on the structure Gly-Gln-Pro-Arg (Rigin) and include its analogues and derivatives thereof. Rigin is a typical tetrapeptide.

The compositions of the disclosed technology may further comprise a pentapeptide, derivatives of thereof, and mixtures thereof. As used herein, "pentapeptide" refers to both the naturally occurring pentapeptide and synthesized pentapeptide. Also useful herein are naturally occurring and commercially available compositions that comprise pentapeptides. Suitable pentapeptides are those chosen from pentapeptide 1, 4, 5, 6, 7, 8, 9, 10, 11, 12, 13, 14, 15, 16, 17, 18, 19, 21, 22, 23, 24, 25, 26, 28, 29, 30, 31, 33, 34, 35, 36, 38, 39, derivatives thereof and mixtures thereof.

The peptide when present in the composition disclosed herein may be present at 0 or 0.01% to 20%, or 0.05% to 15%, or 0.05 to 10 wt % of the composition.

Matrix Metalloproteinase Inhibitor (MMPi)

The term "matrix metalloproteinase inhibitor" relates to all molecule and/or plant or bacterial extracts having an inhibitory activity on at least one of the matrix metalloproteinases expressed, synthetized, or activated by or in the skin. The family of the matrix metalloproteinases is formed of several well-defined groups on the basis of their resemblance regarding structure and substrate specificity (Woessner J. F., Faseb Journal, vol. 5, 1991, 2145).

The MMPi may be present at a level of from 0 or 0.01% to 10%, or 0.1% to 5% or 0.25% to 2.5%, or 0.5% to 1% by weight of the composition.

Whitening Agent

In one embodiment the composition disclosed herein further comprises a whitening/lightening agent.

When the composition further comprises the whitening/lightening agent it may be present at 0 or 0.001 to 10 wt %, or 0.01 to 5 wt %, or 0.1 to 2 wt %, or 0.2 to 1 wt % of the composition. For example the whitening/lightening agent may be present at 0 or 0.001% to 3 wt %, or 0.01 to 2 wt %, or 0.05 to 1 wt %, or 0.1% to 0.5 wt % of the composition.

The whitening/lightening may include at least one of the following ingredients: *Emblica*, Mulberry leaf extract, mangostin, *Sophora*, a flavonoid, hydroxyphenoxy propionic acid and dimethylmethoxy chromanol.

In one embodiment the whitening/lightening agent may be a mixture of ingredients chosen from: *Emblica* and *Sophora*, optionally in the presence of Mulberry leaf extract. For example the Mulberry leaf extract may be present.

The *Emblica* may be *Emblica officinalis*, for example comprising over 40% by weight (for example 50-80 wt %) of Emblicanin A. Emblicanin B, Pedunculagin and Punigluconin, and not more than about 1% by weight of flavonoids. The *Emblica* may be *phyllanthus Emblica*.

The *Sophora* may be an extract of a small tree, and shrub in the pea family Fabaceae.

For example The *Emblica* may be *phyllanthus Emblica* and *Sophora* may be derived from *Sophora Angustifolia* Root Extract.

The flavonoid species is believed to have antioxidant performance, and be an antioxidant plant polyphenolic agent. By the term antioxidant plant polyphenolic agent we mean a plant extract, or a derivative thereof, comprising flavonoid species, including flavones, flavonols, flavanones, flavanols anthrocyanidins and isoflavonoids; phenolic acid species; stilbenes; and lignans, which provide an antioxidant benefit. Antioxidant benefit is measured using the total antioxidant capacity (TAC) assay described herein. Plants provide a rich source of polyphenolic agents, and are therefore an efficient source of said antioxidants. Similar actives may be prepared synthetically and as such are analogues of said plant polyphenolic agents.

Antioxidant polyphenolic agents (different from the compound having two or more hydroxyl groups, wherein the compound has a molar mass of at least 150 g/mol) may include extracts from plants chosen from Mulberry (e.g. *Morus alba*), Ginseng (e.g. *Panax ginseng*), Raspberry, Oregano (e.g. *Origanum vulgare*), Green tea (e.g. green leaves of *Camellia sinensis*), White tea (e.g. *Camellia sinensis*), Blueberry extract (e.g. *Vaccinium cyanococcus*), French maritime pine bark (e.g. *Pinus pinaster*, sold under the trade name Pycnogenol), Rosemary (e.g. *Rosmarinus officialis*), Grape, including grape seed (e.g. *Vitis vinifera*), Fennel (e.g. *Foeniculi fructus*), *Caragana sinica*, Marjoram (e.g. *Origanum majorana*), Crocus (e.g. *Crocus sativus*), Apple (e.g. *Malus domestica*), Coffee, Green coffee, Cherry (e.g. *Prunus avium*), Snow algae (e.g. *Chlamydomonas nivalis*), Emblica (e.g. *Phyllanthus emblica*), Gingko (e.g. *Gingko biloba*), Moringa (e.g. *Moringa oleilera*), Ginger (e.g. *zingiberaceae*), Magnolia (e.g. *Magnolioideae virginiana*), French saffron, Edelweiss (e.g. *Leontopodium alpinium*), White lotus (e.g. *Nymphaea alba*), Turmeric root, Marshmallow (e.g. *Althaea officianlis*), Burdock (e.g. *Arctium lappa*), Bilberry (e.g. *Vaccinium myrtillus*), Cranberry (e.g. *Vaccinium oxycoccus*), Pomegranate nectar (e.g. *Punica granatum*), Sage (e.g. *Salvia officinalis*), Thyme (e.g. *Thymus vulgaris*), Sunflower (e.g. *Helianthus annuus*), wild carrot (e.g. *Daucus carota*), Hop (e.g. *Humulus lupulus*), Witch Hazel (e.g. *hamamelis*), Oak (e.g. *Quercus*), Camellia (e.g. *theacea*), Red clover (e.g. *Tritolium pratense*), Flax (e.g. *Linium usitatissimum*), lemon (e.g. *Citrus limon*), birch (e.g. *betula*), cornflower, (e.g. *Centaurea cyanus*), geranium, *polygonum*, soy (e.g. *Glycine max*), and mixtures thereof.

In one embodiment the antioxidant polyphenolic agent may be an extract from a plant chosen from mulberry, ginseng, grape, oregano, grape, sage, sunflower, maritime pine bark, rosemary, marjoram, *crocus*, french saffron, wild carrot, hop, coffee, green coffee, witch hazel, oak, *camellia*, red clover, flax, ginger, *magnolia*, edelweiss, burdock and mixtures thereof.

Active polyphenolic species sourced from the above list of plants include those chosen from apigenin, luteolin, quercetin, kaempferol, naringenin, hesperetin, catechin, gallocatechin, cyaniding, pelargonidin, daidzein, caffeic acid, chlorogenic acid, romsmarinic acid, gallic acid, resveratrol, ferulic acid, epigallocatechin gallate, piceatannol, secoisolariciresinol, isotaxiresinol, Miyabenol c, Luteolin and mixtures thereof.

The amounts of antioxidant plant polyphenolic agents used in the presently disclosed technology are expressed as dry weights of the extract, as understood by a man skilled in the art. The antioxidant plant polyphenolic agent (plant extract) may be present at 0.005 to 10 wt, or 0.01 to 7 wt %, or 0.01 to 5 wt % of the composition.

When present the chromane may be chosen from: methyl, di-, tri- and tetra-C1-C6 alkyl, C1-C6 alkoxy chromanol; pentamethyl chromanol, methyl, di, tri and tetra C1-C6 alkyl, C1-C6 alkoxy chromanyl C14-C20 ester and mixtures thereof.

The chromane may be chosen dimethyl methoxy chromanol, tetramethyl methoxy chromanol, pentamethyl chromanol, dimethyl methoxy chomanyl palmitate, dialkyl methoxy chomanyl myristate, dimethyl methoxy chromanyl stearate, dimethyl methoxy chomanyl oleate, dimethyl methoxy chomanyl linoleate and mixtures thereof.

In one embodiment the chromane may be dimethyl methoxy chromanol (commercially available under the trade name Lipochroman 6 as sold by Lipotec).

Skin Conditioning Agent

The composition disclosed herein may optionally comprise a skin conditioning agent. The skin conditioning agents may be chosen from humectants, emollients, moisturisers, or mixtures thereof. Where present, the skin conditioning agent may be present from 0.01 to 20 wt %, or 0.1 to 10 wt %, or 0.5 to 7 wt % of the composition.

The skin conditioning agents may be chosen from guanidine, urea, glycolic acid and glycolate salts, lactic acid and lactate salts, aloe vera, shea butter, polyhydroxy alcohols, such as sorbitol, mannitol, xylitol, erythritol, glycerol, hexanetriol, butanitriol, (di) propylene glycol, butylene glycol, hexylene glycol, polyethylene glycol, sugars (e.g. fructose, glucose, xylose, honey, mannose, xylose), gluconodeltalactone, and starches and their derivatives, pyrrolidone, carboxylic acid, hyaluronic acid and salts thereof, lactamide monoethanolamine, acetamide monoethanolamine, panthenol, allantoin and mixtures thereof.

For example the skin conditioning agent may be chosen from glycerine, arabinoglactan, butylene glycol, hyaluronic acid, shea butter, propylene glycol, ethylhexyl glycerine, hyaluronate and mixtures thereof.

Sunscreen

The composition disclosed herein may optionally comprise a sunscreen component. The sunscreen may include organic or inorganic sun filters or a combination of the two. Suitable inorganic sunfilters include those chosen from microfine titanium dioxide, and microfine zinc oxide, and mixtures thereof.

Suitable organic sunscreens include those chosen from: a) p-aminobenzoic acids, their esters and derivatives (for example, 2-ethylhexyl p-dimethylaminobenzoate), b) methoxycinnamate esters (for example, 2-ethylhexyl p-methoxycinnamate, 2-ethoxyethyl p-methoxycinnamate or a, p-di-(p-methoxycinnamoyl)-a'-(2ethylhexanoyl)-glycerin, c) benzophenones (for example oxybenzone), d) dibenzoylmethanes such as 4-(tert-butyl)-4'-methoxydibenzoylmethane, e) 2-phenylbenzimidazole-5 sulphonic acid and its salts, f) alkyl-ss, ss-diphenylacrylates for example alkyl a-cyano-ss, ss-diphenylacrylates such as octocrylene, g) triazines such as 2,4,6-trianilino-(p-carbo-2-ethyl-hexyl-1-oxi)-1,3,5 triazine, h) camphor derivatives such as methylbenzylidene camphor and i) mixtures thereof. Other sunscreen ingredients include those chosen from homosalate, Ethylhexyl salicylate, Diethylhexylbutamido triazone, Bisethylhexyloxyphenol methoxyphenyl triazine, Diethylamino hydroxybenzoyl hexyl benzoate, Butyl methoxydibenzoylmethane, Methylene bis-benzotriazoyl tetramethylbutylphenol, Polysilicone-15 and mixtures thereof. A sunscreening agent may be present from 0 to 10 wt %, or 0.1 to 10 wt % of the composition.

Other Optional Ingredients

The compositions disclosed herein may also optionally comprise one or more of the following optional ingredients. Preservatives may be added to the composition such as benzoic acid, sodium benzoate, sorbic acid, potassium sorbate, 2-bromo2-nitropropane-1,3-diol (bronopol, commercially available under the trade name Myacide®), benzyl alcohol, diazolidinyl urea, imidazolidinyl urea, methyl paraben, phenoxyethanol, ethyl paraben, propyl paraben, sodium methyl paraben, sodium dehydroacetate, polyhexamethylenebiguanide hydrochloride, isothiazolone and sodium propyl paraben and mixtures thereof, suitably in an amount of from 0.01 to 10 wt % of the composition.

Sequestering agents may be added to the composition, such as ethylenediamine tetraacetic acid and salts thereof, for example in an amount of from 0.005 to 0.5 wt % of the composition.

The composition may also include waxes such as cocoa butter suitably in an amount of from 0.1 to 10 wt % of the composition.

The composition may include suitable, cosmetically acceptable diluents, carriers and/or propellants such as dimethyl ether. The composition may also include pearlising agents such as stearic monoethanolamide and/or mica, suitably in an amount of from 0.01 to 10 wt % of the composition.

Perfumes may be added suitably in an amount of from 0.01 to 2 wt % of the composition, as may water soluble dyes such as tartrazine, suitably in an amount of from a trace amount such as $1\times10^{-5}$ to 0.1 wt % of the composition.

The composition may also include pH adjusting agents such as sodium hydroxide, amino methyl propanol, triethanolamine, suitably in an amount of from 0.01 to 10 wt % of the composition. The composition may be buffered by means well known in the art, for example by use of buffer systems comprising succinic acid, citric acid, lactic acid, and acceptable salts thereof, phosphoric acid, mono- or disodium phosphate and sodium carbonate. Suitably, the composition may have a pH between 3 and 10, between 4 and 8, or between 4.5 and 6.5.

In one embodiment the composition of the disclosed technology does not contain an ascorbic acid derivative chosen from sodium ascorbyl phosphate, ascorbyl glycoside, L-ascorbic acid, ascorbyl palmitate, retinyl ascorbate, tetrahexyldecyl ascorbate, or magnesium ascorbyl phosphate.

In one embodiment the composition of the disclosed technology does not include MMPi compounds that comprise one hydroxyaryl or polyhydroxyaryl compound, or cyclic compounds having a cyclic group based upon a compound comprising a pyran, a lactam, or a piperidine constituent.

Cosmetically Acceptable Medium

The cosmetically acceptable medium comprises an aqueous phase. The medium may also comprise, alcohol, and/or an oil. In one embodiment the cosmetically acceptable medium may include water and/or an oil.

The composition disclosed herein may be in the form of a gel or an emulsion.

As used herein reference to gel is used in the ordinary sense defined by IUPAC and is intended to include a non-fluid colloidal network or polymer network that is expanded throughout its whole volume by a fluid. The fluid may for instance be water or alcohol. In one embodiment the fluid may be water.

When the composition disclosed herein is in the form of an emulsion, the emulsion disclosed herein may be a waterin-oil, oil-in-water, or water-in-silicone composition, for example an oil-in-water, or water-in-silicone composition, often oil-in-water.

The emulsion may include an oil phase and have an aqueous phase content of 10 to 90 wt %, or 30 to 85 wt %, or 40 to 80 wt %, or 50 to 75 wt % of the composition.

The emulsion may include an oil phase having 15 to 70 wt %, or 10 to 60 wt %, or 20 to 50 wt %, or 25 to 50 wt %, or 40 of the composition.

The emulsion may be an oil-in-water composition comprising 15 to 70 wt % of an oil phase; and 30 to 85 wt % of an aqueous phase, or comprising 25 to 50 wt % of an oil phase; and 50 to 75 wt % of an aqueous phase.

In one embodiment when the composition is in the form of an oil-in-water emulsion that the aqueous phase may be present at 40 to 90 wt %, and the oil phase may be present at 10 to 60 wt % of the composition.

The emulsion may be in the form of a water-in-silicone emulsion, and the water phase may be present at 30 to 85 wt % of an aqueous phase; and silicone present at 15 to 70 wt % of a silicone phase.

The emulsion may be in the form of a water-in-silicone emulsion, and the water phase may be present at 60 to 75 wt % of an aqueous phase; and silicone present at 25 to 40 wt % of a silicone phase.

If the composition disclosed herein is in the form of a water-in-silicone composition the oil phase may be provided by any suitable silicate, dimethiconols, silicone elastomer and mixtures thereof (for example a silicone elastomer).

For example the silicone oil phase may be formed from an organopolysiloxane. The organopolysiloxane may be chosen from one or more of a polyalkylsiloxane, alkyl substituted dimethicone, cyclomethicone, trimethylsiloxysilicate, dimethiconol, polyalkylaryl siloxane, and mixtures thereof. The polyalkylsiloxane may be for example a cyclomethicone, or dimethicone, for example a dimethicone.

A water-in-silicone composition disclosed herein may include an emulsifying cross-linked organopolysiloxane elastomer, a non-emulsifying cross-linked organopolysiloxane elastomer, or a mixture thereof. The term "non-emulsifying," as used herein, defines cross-linked organopolysiloxane elastomers from which polyoxyalkylene units are absent. The elastomers may include dimethyl polysiloxanes cross-linked by Si—H sites on a molecularly spherical MQ resin. Emulsifying cross-linked organopolysiloxane elastomers include the cross-linked polymers described in U.S. Pat. Nos. 5,412,004; 5,837,793; and 5,811,487. The emulsifying elastomer comprised of dimethicone copolyol crosspolymer (and) dimethicone commercially available from Shin Etsu under the trade name KSG-21.

The non-emulsifying elastomers may include dimethicone crosspolymers. Such dimethicone crosspolymers are supplied by a variety of suppliers including Dow Corning (EL9240). Other dimethicones crosspolymer are available from General Electric (SFE 839), Shin Etsu (KSG-15, 16, 18 [dimethicone/phenyl vinyl dimethicone crosspolymer]), and Grant Industries (GRANSIL™ line of elastomers). Cross-linked organopolysiloxane elastomers useful in the composition disclosed herein and processes for making them are further described in U.S. Pat. Nos. 4,970,252; 5,760,116; and 5,654,362. Commercially available elastomers typical for use herein are Dow Corning's 9040 silicone elastomer blend, Shin Etsu's KSG-21, and mixtures thereof.

An oil-in-water or water-in-oil emulsion may include an organic oil. The organic oil may be volatile or non-volatile. The organic oil may include a diluent, a solvent, a polyolefin polymer, or an ester oil.

The term "ester oil" means an oil that is liquid at room temperature (25° C.) comprising at least one ester functional group. The ester oil used herein is chosen, for example, from monoesters.

The ester oil may, for example, be chosen from the monoesters of formula $R^1COOR^2$ wherein $R^1$ may be selected from linear and branched hydrocarbon-based chains comprising from 4 to 30, or 6 to 24, or 7 to 20 carbon atoms carbon atoms, and $R^2$ may be chosen from branched hydrocarbon-based chains comprising from 3 to 40 carbon atoms, such as from 10 to 30 carbon atoms and further such as from 16 to 26 carbon atoms.

Examples of the ester oils that may be mentioned include isodecyl neopentanoate; isocetyl octanoate; isononyl isononanoate, isodecyl isononanoate, tridecyl isononanoate; hexyl laurate, 2-hexyldecyl laurate; isopropyl myristate, isocetyl myristate, isotridecyl myristate, 2-octyldodecyl myristate; isopropyl palmitate, 2-ethylhexyl palmitate, isooctyl palmitate, isocetyl palmitate, isodecyl palmitate, isostearyl palmitate, 2-octyldecyl palmitate; isopropyl isostearate, 2-octyldodecyl stearate, isostearyl isostearate, and 2-octyldodecyl erucate.

The ester oil may be present in the emulsion disclosed herein in an amount ranging, for example, from 0 to 20 wt %, or 0.1 to 15 wt %, or 1 to 10 wt % of the composition.

EXAMPLES

A series of compositions are prepared using the following general procedure. A percentage of water is added to a vessel, and a percentage of salicylic acid is added to form a mixture. The mixture is then stirred for approximately 30 minutes. A percentage of Vitamin C, or a derivative thereof is added to the vessel and stirred until it is dissolved. The pH is adjusted to 4.5±0.1 using a 50 w/w solution of either potassium hydroxide or citric acid powder. The compositions prepared are:

Comparative Example 1 (CE1): a composition containing 0.2 wt % of sodium ascorbyl phosphate, and 2 wt % of salicylic acid.

Comparative Example 2 (CE2): a composition containing 0.2 wt % of ascorbyl glucoside, and 2 wt % of salicylic acid.

Inventive Example 1 (IE1): a composition containing 0.2 wt % of 3-O-ethyl ascorbic acid, and 2 wt % of salicylic acid.

Testing

The examples are evaluated for stability by analysis of colour changes over time using an X-Rite Color™ i7 Benchtop Spectrophotometer with transmission kit for liquid measurements. The test procedure involves the following steps for each new sample: (1) Calibrate spectrophotometer for transmission measurement, (2) Fill cuvette with test solution, (3) Insert cuvette into instrument, (4) Measure initial (standard) L*a*b* values for each example, and (5) Clean and dry solution for next measurement.

After initial measurement each example is placed in a humidity cabinet at 40° C. The changes in colour are measured for each example after 1, 7 and 14 days after each sample is stored in a cabinet at 40° C. Prior to colour change measurements each sample is allowed to cool to 23° C. Each example is then evaluated by the following steps 1-5 above.

The DE2000 rating after initial measurement in the spectrophotometer is normalised to be 0. The results obtained after 1, 2, 3, 4, and 8 weeks for each example are shown in the following tables for measurements made at 3° C., 23° C., and 40° C. Typically better results are obtained for examples having a lower DE2000 rating (DE2000 is unitless measure of colour change). An increase in DE2000 indicates an example is becoming less stable over time.

| | DE2000 Measurement at 3° C. | | |
|---|---|---|---|
| Time/weeks | IE1 | CE1 | CE2 |
| 0 | 0 | 0 | 0 |
| 1 | 0.09 | 0.11 | 0.11 |
| 2 | 0.09 | 0.09 | 0.1 |
| 3 | 0.05 | 0.08 | 0.09 |
| 4 | 0.08 | 0.11 | 0.13 |
| 8 | 0.09 | 0.08 | 0.18 |

| | DE2000 Measurement at 23° C. | | |
|---|---|---|---|
| Time/weeks | IE1 | CE1 | CE2 |
| 0 | 0 | 0 | 0 |
| 1 | 0.08 | 0.14 | 0.11 |
| 2 | 0.1 | 0.25 | 0.1 |
| 3 | 0.08 | 0.43 | 0.09 |
| 4 | 0.1 | 0.63 | 0.13 |
| 8 | 0.1 | 1.12 | 0.18 |

| | DE2000 Measurement at 40° C. | | |
|---|---|---|---|
| Time/weeks | IE1 | CE1 | CE2 |
| 0 | 0 | 0 | 0 |
| 1 | 0.09 | 1.76 | 0.1 |
| 2 | 0.08 | 2.38 | 0.06 |
| 3 | 0.09 | 3.5 | 0.11 |
| 4 | 0.11 | 3.97 | 0.13 |
| 8 | 0.21 | 5.89 | 0.27 |

The results obtained indicate that the composition of the disclosed technology has improved stability at 3° C., 23° C., and 40° C. compared to comparative examples containing Vitamin C, or derivatives thereof (such as sodium ascorbyl phosphate, and ascorbyl glucoside).

We claim:

1. A composition comprising:
0.1 to 3 wt % of an aromatic beta hydroxy acid;
0.05 to 2.5 wt % of an O-substituted ascorbic acid represented by the formula:

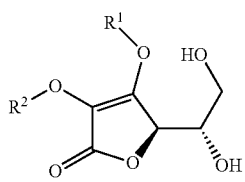

wherein $R^1$ and $R^2$ groups are independently H, C1-20 alkyl, C3-20 cycloalkyl, C1-20 alkoxy, C2-20 acyl, C6-20 aryl, C1-20 heterocyclic aromatic, C1-20 heterocyclic non-aromatic, or C3-20 cycloalkenyl with the proviso that both R1 and R2 cannot be H; and
a cosmetically acceptable medium comprising an aqueous phase,
wherein the aromatic beta hydroxy acid is present at a higher concentration than the O-substituted ascorbic acid and the composition has a pH value between 3.0 and 5.5.

2. The composition of claim 1, wherein the O-substituted ascorbic acid is 3-alkyl ascorbic acid.

3. The composition of claim 2, wherein the O-substituted ascorbic acid is 3-O-alkyl ascorbic acid.

4. The composition of claim 1, wherein the aromatic beta hydroxy acid is salicylic acid.

5. The composition of claim 1, wherein the composition comprises 1 to 2.5 wt % of the aromatic beta hydroxy acid and 0.09 to 2.5 wt % of the O-substituted ascorbic acid.

6. The composition of claim 1, wherein the composition has a weight ratio of the aromatic beta hydroxy acid to the O-substituted ascorbic acid of (i) 1:less than 1 to 1:0.01, or (ii) 1:0.7 to 1:0.5 or (iii) 1:0.5 to 1:0.1.

7. The composition of claim 1, wherein the emulsion is an oil-in-water emulsion and the oil-in-water emulsion has an aqueous phase present at 40 to 90 wt % of the composition, and optionally wherein the oil phase is present at 10 to 60 wt % of the composition.

8. The composition of claim 1, wherein the composition does not include gluconolactone.

9. The composition of claim 1, wherein the composition has a pH ranging from 4.0 to 5.5.

10. The composition of claim 1, wherein the composition comprises 0.5 to 2.5 wt % of the aromatic beta hydroxy acid.

11. The composition of claim 1, wherein the composition comprises 0.09 to 2.5 wt % of the O-substituted ascorbic acid.

12. The composition of claim 1, wherein the composition does not include ascorbyl glucoside.

13. The composition of claim 1, wherein the composition does not include an ascorbic acid derivative chosen from sodium ascorbyl phosphate, ascorbyl glucoside, L-ascorbic acid, ascorbyl palmitate, retinyl ascorbate, tetrahexyldecyl ascorbate, or magnesium ascorbyl phosphate.

14. A method of improving skin care comprising administering to skin a composition of claim 1, wherein improving skin care includes (i) improving skin exfoliation, or moisturisation, or (ii) decreasing or preventing at least one of the following: forming wrinkles or fine lines, skin sagging, or hyperpigmentation, or (iii) increasing skin firmness or skin laxity.

* * * * *